United States Patent [19]
Goodley

[11] Patent Number: 4,580,554
[45] Date of Patent: Apr. 8, 1986

[54] TRACTION DEVICE

[76] Inventor: Paul Goodley, 2210 W. 3rd St., Los Angeles, Calif. 90057

[21] Appl. No.: 555,814

[22] Filed: Nov. 28, 1983

[51] Int. Cl.[4] ............................ A61F 5/00; A61H 1/02

[52] U.S. Cl. ........................................ 128/69; 128/71; 128/75

[58] Field of Search ........................ 128/69, 75, 71, 70, 128/73, 68; 272/126, 137, 143

[56] References Cited

U.S. PATENT DOCUMENTS

| | | | |
|---|---|---|---|
| 2,160,722 | 5/1939 | Cunningham | 272/137 |
| 2,633,124 | 3/1953 | Yellin | 128/75 |
| 2,893,384 | 7/1959 | Chick | 128/75 |
| 2,910,061 | 10/1959 | Rabjohn | 128/75 X |
| 2,954,026 | 9/1960 | Spinks | 128/75 |
| 3,605,731 | 9/1971 | Tigges | 128/78 |
| 4,407,274 | 10/1983 | Goodly | 128/69 |

*Primary Examiner*—Richard J. Apley
*Assistant Examiner*—Kathleen D'Arrigo
*Attorney, Agent, or Firm*—Edward A. Sokolski

[57] ABSTRACT

A traction device in which the user himself applies the traction force. A harness runs under the user's body to the dorsal and lumbar region thereof. A strap is attached to the harness and is used to apply traction thereto, the opposite ends of the strap being attached to the ends of a traction bar. The traction bar has attachment means at its center and to the left and right of center, a line or cable being selectively attached to one of these attachment means. This line fits through a suitable fitting and is attached to a force indicator device which is within the user's view. A line runs from the indicator device to a force input drive member adapted to be engaged by the user's feet or hands. In using the device, the user applies the desired amount of force to the force input drive member, as indicated on the indicator device, this force being delivered to a selected portion of the user's back through a suitable applicator member.

8 Claims, 5 Drawing Figures

FIG. 1
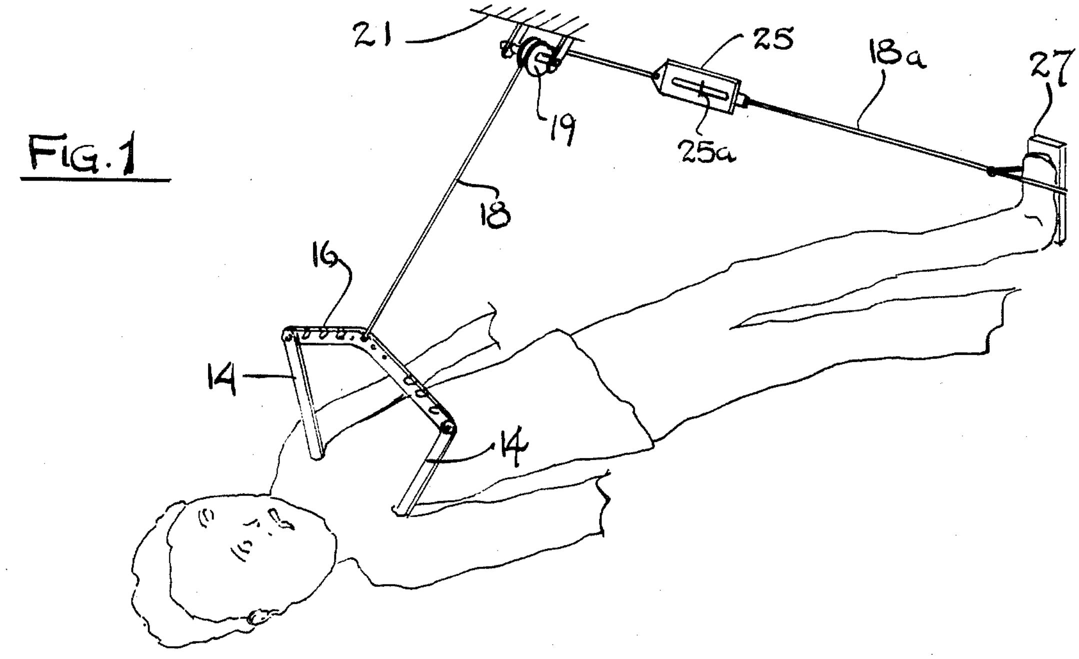
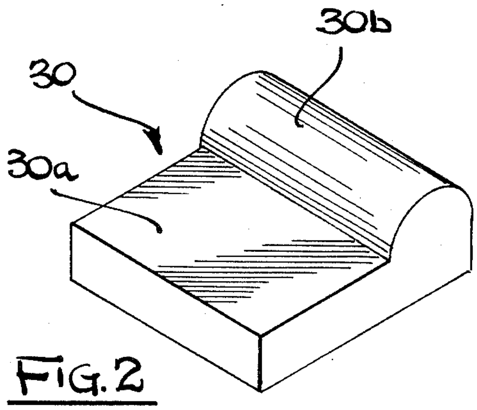
FIG. 2
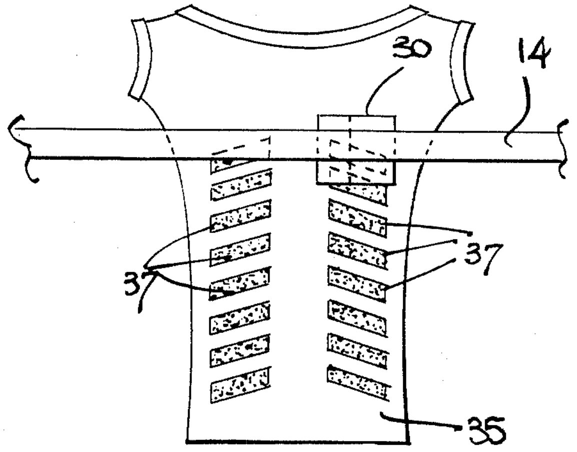
FIG. 4
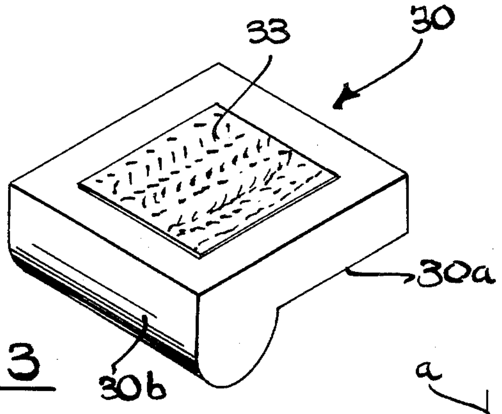
FIG. 3
FIG. 5
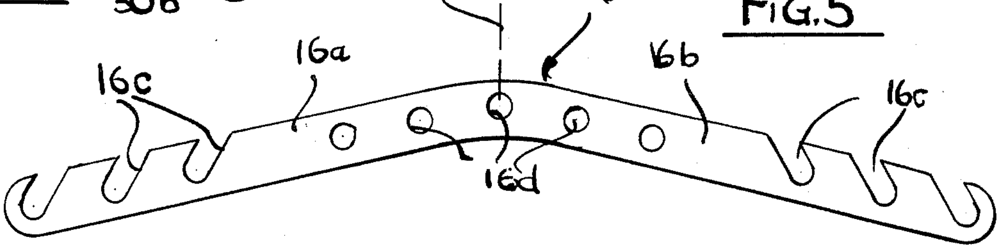

TRACTION DEVICE

This invention relates to a traction device, and more particularly to such device in which the user himself applies traction force to a selected portion of his back.

In my U.S. Pat. No. 4,407,274, a cervical traction device is described for applying traction to the cervical spine through a harness which fits against the user's occiput and neck. In this device, a traction strap is employed, this traction strap being removably attached to the harness at a preselected position therealong which may be in the center to provide neutral rotation, or to the left or right of center to provide rotation either to the left or right, as the particular situation may require. The ends of the strap are attached to the opposite ends of a traction bar, this traction bar having attachment means both at the center thereof and at various positions to the left and right of center. A line, which may be of webbing, rope or cable, is attached to the traction bar at one of the attachment positions thereof, the central attachment position providing symmetrical traction, while asymmetrical traction of various degrees can be applied by attachment to other positions to the left or right of center. The line fits through a suitable fitting and is attached to a force indictor device, the scale of which is within the user's view. A line runs from the opposite end of the indicator device to a force input drive member which is adapted to be engaged by the user's foot. In using this device, the user applies the desired amount of force to the force input drive member, as indicated on the indicator device, this force being delivered to the neck as prescribed by the doctor, either symmetrically or asymmetrically, with or without rotation, and with selected degrees of flexion and lateral bending.

The device of the present invention is a modification of the device of my aforementioned prior application, in which the traction force, rather than being applied to the neck of the user, is applied to the user's back. In the device of the present invention, the same type traction bar (but generally larger), force indicator, force input drive member and interconnecting parts are employed as in the device of my prior application, and insofar as the disclosure of these parts and mechanisms is concerned, my prior U.S. Pat. No. 4,407,274 is incorporated herein by reference. In the device of the present application, means are provided to apply rotary traction force to a selected portion of the user's back, such as the thoracic vertebrae and ribs, or the lumbar vertebrae and sacrum. The traction force is applied by means of a strap attached to the opposite ends of a traction bar with a pressure applicator member mounted on the strap for applying pressure to the selected portions of the user's back. A vest, which may be worn by the user, with suitable markings thereon may be employed for locating the pressure applicator member as prescribed by the physician.

It is therefore an object of this invention to provide an improved traction device for use by a patient wherein he himself, by his own force, can apply the required amount of traction to a selected portion of his back.

It is a further object of this invention to provide a traction device employing an adjustable harness and traction bar which can be adjusted to provide both rotation and asymmetrical traction to a selected portion of the user's back in accordance with medical requirements.

Other objects of the invention will become apparent as the description proceeds in connection with the accompanying drawings of which:

FIG. 1 is a perspective view illustrating an embodiment of the device of the invention;

FIG. 2 is a perspective view illustrating an applicator member which may be employed in the device of the invention;

FIG. 3 is a perspective view of the applicator member of FIG. 2 taken from the opposite side thereof;

FIG. 4 is a schematic view illustrating the use of a jacket member in locating the position of the applicator member; and FIG. 5 is an elevational view of a traction bar which may be employed in the device of the invention.

Referring now to the figures, a preferred embodiment of the invention is illustrated. The opposite ends of traction strap 14 are removably attached to the arms **16*a* and 16*b* of traction bar 16, either at the ends thereof or at other attachment points, 16*c*, therealong (see FIG. 5). Attached to bar 16 through one of apertures 16*d* formed therein, which either may be at the center thereof or to the left or right of center depending upon whether symmetrical or asymmetrical traction is desired, is a traction line or strap 18. Line 18 runs through pulley 19 which is suitably anchored by means of an anchoring device 21. Cable 18 is attached to force indicator 25 which as a scale 25*a* thereon which indicates the force applied to strap 18. The other end of force indicator 25 is connected by means of line 18*a* to a force input drive member 27** which may be in the shape of a bar with foot straps suitable for receiving the feet (or hands) of the user in force applying relationship. This is as described in my aforementioned U.S. Pat. No. 4,407,274.

Traction strap 14 fits around the back of the user and has a force applicator member 30 attached thereto by means of a Velcro fastener 33 as best can be seen in FIGS. 2–4. Force applicator member 30 has a flat portion **30*a* and a rounded raised portion 30*b*, the rounded portion 30*b* fitting conveniently along the user's back in grasping manner. Force applicator 30 is positioned by the physician in the desired location for the application of the needed traction force. Such positioning of the applicator member can be facilitated for home use by the patient by means of special vest 35 which the user wears and which has a series of markers 37 positioned therealong. Thus, the physician can indicate to the patient at which particular marker member 37** the force is to be applied, and the patient can then easily achieve the proper positioning of the applicator member on his own.

While the invention has been described and illustrated in detail, it is to be clearly understood that this is intended only by illustation and example only and is not to be taken by way of limitation, the spirit and scope of the invention being limited only by the terms of the following claims.

I claim:

1. A traction device for use in applying traction to a selected portion of the user's back comprising:
   - traction strap means positioned against a preselected portion of the user's back for applying force to said back portion, the opposite ends of said strap means extending out to the front of the user's body;
   - traction bar means positioned in front of the user's body;

attachment means for removably attaching each of the ends of the traction strap means to said traction bar means at preselected positions near the opposite ends thereof;

line means attached to said traction bar means at a preselected position therealong;

a force indicator device positioned within view of the user attached at one end to said line means;

second line means attached at one end thereof to the other end of the force indicator device;

force input drive means attached to the other end of the second line means for receiving a force input from the user; and applicator means removably attached to said traction strap means and interposed between said strap means and the user's back for applying force against a preselected protion of the user's back;

whereby the force applied by the user to said force input drive means is applied to the user's back in a predetermined symmetrical or asymmetrical manner which is in accordance with the preselected attachment positions of the line means and the ends of the traction strap means to the traction bar means, and the position of attachment of said applicator means to the traction strap means.

2. The device of claim 1 wherein the traction bar has apertures in the center thereof and to left and right of center for use in selectively attaching the line means to said preselected position therealong.

3. The device of claim 1 wherein said traction bar means has a plurality of spaced grooves defining said preselected positions near the opposite ends thereof for use in attaching the attachment means to the traction bar.

4. The device of claim 3 wherein said traction bar comprises a flat bar having a pair of arms forming a wide "V".

5. The device of claim 1 wherein said force indicator device comprises a pair of slidably engaging concentric casing portions fitted together telescopically, and spring means mounted in the inner one of said casing portions for resiliently urging said casing portions towards each other, and scale means on one of said casing portions whereby when a force is applied between the casing portions said casing portions are drawn apart against the force of the spring means to provide an indication of the applied force on said scale means.

6. The device of claim 1 wherein said force input drive means comprises a member in the general shape of a bar having strap attachment means at its center and straps supported thereon and adapted for engagement by the feet or hands of the user for applying traction.

7. A traction device for use in applying traction to a selected portion of the user's back comprising:

traction strap means positioned against a preselected portion of the user's back for applying force to said back portion, the opposite ends of said strap means extending out to the front of the user's body;

traction bar means positioned in front of the user's body;

attachment means for removably attaching each of the ends of the traction strap means to said traction bar means at preselected positions near the opposite ends thereof;

line means attached to said traction bar means at a preselected position therealong;

a force indicator device positioned within view of the user attached at one end to said line means;

second line means attached at one end thereof to the other end of the force indicator device;

force input drive means attached to the other end of the second line means for receiving a force input from the user; and applicator means removably attached to said traction strap means; and interposed between said strap means and the user's back for applying force against any desired portion of the user's back, said applicator means comprising an applicator member having a raised rounded portion which fits against the user's back in a grasping manner;

whereby the force applied by the user to said force input drive means is applied to the user's back in a predetermined symmetrical or asymmetrical manner which is in accordance with the preselected attachment positions of said line means and the ends of the traction strap means to the traction bar means, and the position of attachment of said applicator means to the traction strap means.

8. A traction device for use in applying traction to a selected portion of the user's back comprising:

traction strap means positioned against a preselected portion of the user's back for applying force to said back portion, the opposite ends of said strap means extending out to the front of the user's body;

traction bar means positioned in front of the user's body;

attachment means for removably attaching each of the ends of the traction strap means to said traction bar means at preselected positions near the opposite ends thereof;

line means attached to said traction bar means at a preselected position therealong;

a force indicator device positioned within view of the user attached at one end to said line means;

second line means attached at one end thereof to the other end of the force indicator device;

force input drive means attached to the other end of the second line means for receiving a force input from the user;

applicator means removably attached to said traction strap means interposed between said strap means and the user's back for applying force against a desired portion of the user's back; and a vest worn by the user, marker means being provided on the vest for use in positioning the applicator means against the desired portion of the user's back;

whereby the force applied by the user to said force input drive means is applied to the user's back in a predetermined symmetrical or asymmetrical manner which is in accordance with the preselected attachment positions of said line means and the ends of the traction strap means to the traction bar means, and the position of attachment of said applicator means to the traction strap means.

* * * * *